United States Patent
Axelrod et al.

(10) Patent No.: US 12,133,769 B2
(45) Date of Patent: Nov. 5, 2024

(54) ULTRASOUND SYSTEM AND METHODS THEREOF FOR GENERATION OF A MORPHING FUNCTION AND ELASTIC PROPERTIES OF A MOVING MEDIUM USING FULL WAVEFORM INVERSION

(71) Applicant: Ikko Health Ltd., Tel Aviv (IL)

(72) Inventors: Ramon Axelrod, Kiryat Ono (IL);
Raanan Dafni, Herzliya (IL)

(73) Assignee: Ikko Health Ltd., Tel Aviv (IL)

( * ) Notice: Subject to any disclaimer, the term of this patent is extended or adjusted under 35 U.S.C. 154(b) by 165 days.

(21) Appl. No.: 18/058,106

(22) Filed: Nov. 22, 2022

(65) Prior Publication Data
US 2023/0157673 A1 May 25, 2023

Related U.S. Application Data

(60) Provisional application No. 63/281,981, filed on Nov. 22, 2021.

(51) Int. Cl.
*A61B 8/08* (2006.01)
*A61B 8/00* (2006.01)
(Continued)

(52) U.S. Cl.
CPC .............. *A61B 8/5207* (2013.01); *A61B 8/44* (2013.01); *G01S 7/52042* (2013.01); *G01S 15/8963* (2013.01)

(58) Field of Classification Search
CPC combination set(s) only.
See application file for complete search history.

(56) References Cited

U.S. PATENT DOCUMENTS 6,659,953 B1  12/2003  Sumanaweera et al.
7,027,927 B2   4/2006  Matsuoka et al.
(Continued)

FOREIGN PATENT DOCUMENTS

CN       112773396 A     5/2021
WO       2022123464 A1   6/2022
WO   WO-2023089598 A1 *  5/2023  ............... A61B 8/44

OTHER PUBLICATIONS

Fang, S., Raghavan, R., & Richtsmeier, J. T. (Apr. 1996). Volume morphing methods for landmark-based 3D image deformation. In Medical Imaging 1996: Image Processing (vol. 2710, pp. 404-415). International Society for Optics and Photonics.

(Continued)

*Primary Examiner* — Daniel Pihulic
(74) *Attorney, Agent, or Firm* — M&B IP Analysts, LLC

(57) ABSTRACT

A system and method for creating ultrasound images of a moving medium is provided. The method includes emitting, by a portion of a plurality of emitters, a plurality of ultrasound waves until a motion of the moving medium below a predetermined threshold is determined, wherein the plurality of ultrasound wave is emitted towards the moving medium; receiving, by a portion of a plurality of sensors, a first plurality of received signals corresponding to the plurality of ultrasound waves; generating a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and performing a wave inversion on the model of the morphing function.

22 Claims, 7 Drawing Sheets

(51) Int. Cl.
  *G01S 7/52* (2006.01)
  *G01S 15/89* (2006.01)

(56) References Cited

U.S. PATENT DOCUMENTS

| | | |
|---|---|---|
| 8,433,114 B2 | 4/2013 | Reisman et al. |
| 8,775,143 B2 | 7/2014 | Routh et al. |
| 9,075,160 B2 | 7/2015 | Childs et al. |
| 9,250,337 B2 | 2/2016 | Forges et al. |
| 9,291,710 B2 | 3/2016 | Debroux et al. |
| 9,495,487 B2 | 11/2016 | Krebs et al. |
| 9,557,430 B2 | 1/2017 | Forges et al. |
| 9,689,671 B2 | 6/2017 | Instanes et al. |
| 10,012,745 B2 | 7/2018 | Krebs et al. |
| 10,028,722 B2 | 7/2018 | Moreau-Gaudry et al. |
| 10,120,087 B2 | 11/2018 | Forges et al. |
| 10,234,552 B1 | 3/2019 | Jazayeri et al. |
| 10,310,123 B2 | 6/2019 | Xu et al. |
| 10,436,927 B2 | 10/2019 | Sun et al. |
| 10,451,726 B1 | 10/2019 | Jazayeri et al. |
| 10,578,755 B2 | 3/2020 | Wang et al. |
| 10,704,901 B2 | 7/2020 | Instanes et al. |
| 10,705,233 B2 | 7/2020 | Xu et al. |
| 10,871,588 B2 | 12/2020 | Beitz et al. |
| 2012/0059633 A1 | 3/2012 | Dutta et al. |
| 2019/0328355 A1 | 10/2019 | Agudo |
| 2020/0003892 A1 | 1/2020 | Jazayeri et al. |
| 2020/0278463 A1 | 9/2020 | Maeki et al. |
| 2020/0391244 A1 | 12/2020 | Willey et al. |
| 2021/0055440 A1 | 2/2021 | Beitz et al. |
| 2021/0080573 A1 | 3/2021 | Bachmann et al. |
| 2021/0215642 A1 | 7/2021 | Fincke et al. |
| 2023/0157673 A1* | 5/2023 | Axelrod ................ A61B 8/485 600/443 |

OTHER PUBLICATIONS

Rohr, K., Stiehl, H. S., Sprengel, R., Buzug, T. M., Weese, J., & Kuhn, M. H. (2001). Landmark-based elastic registration using approximating thin-plate splines. IEEE Transactions on medical imaging, 20(6), 526-534.

Guasch L. et al. "Full-waveform inversion imaging of the human brain" npj Digital Medicine vol. 3, Article No. 28, p. 1-12, (2020) . Mar. 6, 2020 (Mar. 6, 2020).

International Search Report for PCT/IB2022/061296, dated Mar. 20, 2023. International Bureau of WIPO.

Written Opinion of the Searching Authority for PCT/IB2022/061296, dated Mar. 20, 2023. International Bureau of WIPO.

* cited by examiner

ULTRASOUND SYSTEM AND METHODS THEREOF FOR GENERATION OF A MORPHING FUNCTION AND ELASTIC PROPERTIES OF A MOVING MEDIUM USING FULL WAVEFORM INVERSION

CROSS-REFERENCE TO RELATED APPLICATIONS

This application claims the benefit of benefit of U.S. Provisional Application No. 63/281,981 filed on Nov. 22, 2021, the contents of which are hereby incorporated by reference.

TECHNICAL FIELD

The disclosure generally relates to ultrasound imaging system and more particularly to full waveform inversion processing, and furthermore particularly to their use with ultrasound waves on a bodily tissue.

BACKGROUND

Inversion problems aim to calculate from a set of observed signals the causal factor that produces them. It is the inverse of the forward problem which starts with causes and computes the results. The inversion attempts to find the best model that fits the acquired data. In the case of earth's subsurface exploration and medical ultrasound, (ultra)sound waves are emitted from emitters and sensed by sensors placed on the medium's surface. An inversion algorithm may be used to generate high-resolution, models of the medium's elastic properties and attenuation. The accuracy and resolution are gained by exploiting waveform data acquired by multiple simple sensors spread over a large area rather than relying solely on returning echoes of a highly localized sensor array.

Seismic inversion typically refers to a set of algorithms applied to build a model of the earth interior elastic properties by processing data records of measured seismic waves. Most algorithms are based on simulation of the seismic pressure wavefield at receiver locations. The simulated data is matched against the measured data, and the data misfit is inverted into a model update of the elastic properties. The algorithms differ in the way they simulate the wavefields, the wave modes that are selected for inversion and how they alter the model of elastic properties. Algorithms for wave propagation simulation commonly refers to ray tracing theory (or bundle of rays); Kirchhoff or Born modeling approximation; and one- or two-way wave simulation.

Current waveform inversion algorithms rely on the medium being static in time during the data acquisition. However, for various applications this assumption does not hold, and there is some time dependency introduced by short scale movements that cannot and should not be neglected. For example, a patient undergoing a medical examination may continue to breath, slightly move or twist, that can potentially cause inaccuracies in the readings. In the fields of photogrammetry and x-ray corrections there exist algorithms that correct movement by image processing techniques. Such corrections are performed by finding features in the image(s), building a morphing function that describes the movement, and finally correcting the image. Current solutions are based on image processing techniques that require an image to begin with. It should be note noted that the raw data is not an image for inversion problems. To build the image, a morphing function is needed, however, such a morphing function does not exist at that point.

In one field of endeavor, motion during certain types of ultrasound imaging is suggested. In such cases, for example, a first ultrasound image is taken followed by a second ultrasound image. The data of the two images are processed to determine an overlapping region. Preferably, image registration of the images with each other using rigid registration is performed. Thereafter, a non-rigid deformation between the two images, using, for example, an elastic registration algorithm is performed. By applying alpha-morphing on each overlapping region of each image using the non-rigid deformation and obtaining a blend region of the overlapping region by performing an alpha-blending, a clear image at motion may be achieved. Alpha-blending blends the two images by varying the relative contribution of the two image volumes using the results of alpha-morphing. However, this restricts ultrasound operation mode that requires scanning, i.e., motion of the emitters/sensors over the surface, and further requires initial presence of images. Such challenges remain unresolved, as the actual effect of motion may be detrimental to the generation of usable ultrasound images in general, and specifically the first reference ultrasound image.

In another field of endeavor, ultrasound signals are used to provide images from bodily tissues and internal organs. The use of an ultrasound transmitter and receiver requires a degree of technical competency by the user of the transponder that sends and receives the ultrasound waves. The area covered is small and when larger bodily areas need to be covered, the transponder needs to be moved back and forth over the body's surface. Such mobile operations enable scanning of the larger area and further take into account the motion of the transponder as well as changes in position of emitters and sensors.

However, challenges remain as conventional full-waveform inversion (FWI) is not adapted to motion at speeds that are in the order of bodily organ or tissue motion. While analysis may be in an acceptable range when the object (or medium) is still or near still, for various applications, this assumption of stillness, or near stillness, does not hold. A time dependency of short scale movements that cannot be neglected are detected. For example, a patient undergoing a medical examination is still breathing or slightly twisting, and such bodily changes cannot be properly considered.

It would therefore be advantageous to provide solutions that would overcome the shortcomings of the traditional FWI that do not rely on processing an image.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for creating ultrasound images of a moving medium by generating a morphing function. The method comprises emitting, by a portion of a plurality of emitters, a plurality of ultrasound waves until a motion of the moving medium below a predetermined threshold is determined, wherein the plurality of ultrasound wave is emitted towards the moving medium; receiving, by a portion of a plurality of sensors, a first plurality of received signals corresponding to the plurality of ultrasound waves; generating a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and performing a wave inversion on the model of the morphing function.

Certain embodiments disclosed herein also include a non-transitory computer readable medium having stored thereon causing a processing circuitry to execute a process, the process comprising: emitting, by a portion of a plurality of emitters, a plurality of ultrasound waves until a motion of the moving medium below a predetermined threshold is determined, wherein the plurality of ultrasound wave is emitted towards the moving medium; receiving, by a portion of a plurality of sensors, a first plurality of received signals corresponding to the plurality of ultrasound waves; generating a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and performing a wave inversion on the model of the morphing function.

Certain embodiments disclosed herein also include a system for creating ultrasound images of a moving medium by generating a morphing function. The system comprises: a processing circuitry; and a memory, the memory containing instructions that, when executed by the processing circuitry, configure the system to: [complete based on final claims]. a processing circuitry; a plurality of ultrasound emitters adapted to emit an ultrasound wave under control of the processing circuitry; a plurality of ultrasound sensors adapted to send readings corresponding the ultrasound waves received by the plurality of ultrasound sensors; and a memory communicatively connected to the processing circuitry and containing therein a plurality of instructions that when executed by the processing circuitry, configure the system to: emit, by a portion of a plurality of emitters, a plurality of ultrasound waves until a motion of the moving medium below a predetermined threshold is determined, wherein the plurality of ultrasound wave is emitted towards the moving medium; receive, by a portion of a plurality of sensors, a first plurality of received signals corresponding to the plurality of ultrasound waves; generate a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and perform a wave inversion on the model of the morphing function.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
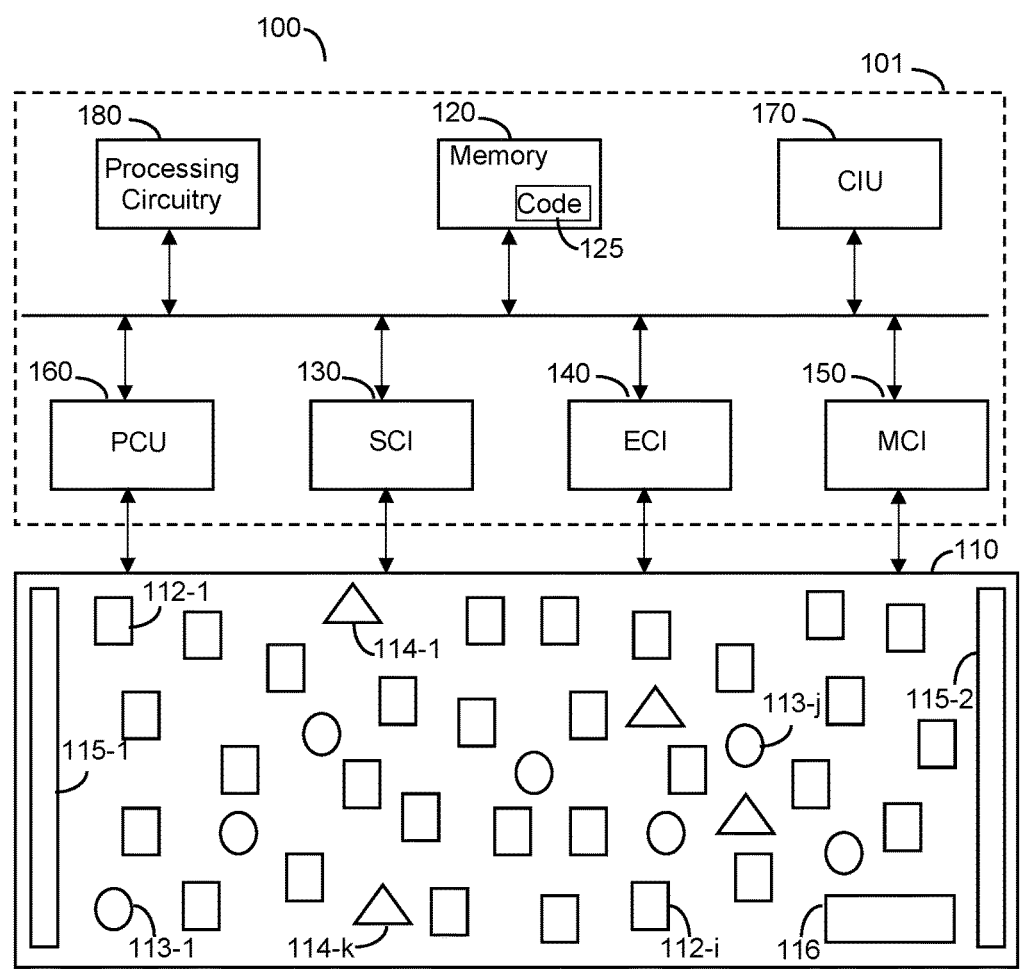
FIG. 1 is a system for performing full waveform inversion in a moving medium according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

An ultrasound system adapted to generate a morphing function is used for generation of ultrasound images of moving mediums. A plurality of emitters and further a plurality of sensors, are both sparsely placed on a surface applied around a moving medium. A changing group of the plurality of emitters repeatedly emit ultrasound waves that are captured by a changing group of the plurality of sensors. An initial model of elastic properties and a morphing function is generated to account for the changes of the medium motion over time. During the inversion process, the morphing function and elastic properties, prior to the generation of ultrasound images, are continuously refined until such time that its accuracy exceeds a predetermined accuracy threshold. The morphing function and elastic properties can then be used in the process of generation of ultrasounds images. To this end, the disclosed embodiments account for motion within the medium and in turn improves ultrasound imaging. It should be noted that the motion within the medium are small motions such as, but not limited to, bowel movement, expansion of blood vessels, raising of the rib case, and the like, and any combination thereof. Moreover, the refinement of the model and the morphing function enables creation of elastic properties model prior to generation of an ultrasound image eliminating a need for an ultrasound image to perform morphing analysis.

According to the disclosed embodiments, portions of the components such as, the emitters, sensors, and the like, are activated to emit and receive ultrasound waves with the moving medium. By activating portions of the components, measurements of a same region may be obtained for verification and improved accuracy. Moreover, the process of generating the model and the morphing function is performed upon detection a small motion below a predetermined threshold. That is, the process may not be performed until acceptable ranges of data indicating small movement are received to reduce processing burden in the system. It should be noted that such partial and/or conditional activation of components provide means for conservation of power and resources in various components of the ultrasound system such as, but not limited to, the emitter, sensor, controller, and the like.

The disclosed embodiments described herein applies to a variety of methods that internally use full wave propagation (e.g., FWI and its variants, Least Squares Migration (LSM), one- or two-way wave equation migration, Reverse Time Migration (RTM), other seismic migration variants, and more) but will be primarily demonstrated with respect of FWI. Ordinary skill in the art would appreciate that migration variants include, for example, but not limited to, least squares migration (LSM), reverse time migration (RTM), and the like, and inversion variants include, for example, but not limited to, FWI, adaptive wave equation (AWI), physically based deep neural networks (DNN) inversion, and other like variants. However, these examples should not be viewed as limiting the scope of the disclosed embodiments whatsoever.

FWI is a method for generating high-resolution elastic models by application of ultrasound waves. The accuracy is gained by the use of the full waveform acquired by multiple simple sensors that are spread over a large area rather than only return echoes of highly localized sensor array. Given an initial model estimation and emitters' signals, the FWI method solves the wave equation to find the expected signal at a plurality of sensors for that model. It then iteratively updates the model to decrease the misfits between calculated and actually acquired signals. According to the disclosed embodiments, FWI is modified to accommodate for the medium being not-static over the time of data acquisition. That is, in an embodiment, a morphing function is generated and incorporated into the FWI to consider motion within the medium. Moreover, the morphing function is continuously refined through iterative modification of a model of the morphing function. It should be noted that the modified FWI refines the model of the morphing function, sound velocity model, and the attenuation model, prior to generation of ultrasound image for improved accuracy without prerequisite images.

FIG. 1 depicts an example system 100 for performing a full waveform inversion (FWI) in a moving medium according to an embodiment. The system 100 comprises of an ultrasound sensing garment (USG) 110 embedded with sensors 112 (sensors 112-1 through 112-$i$, where 'i' is an integer greater than '1'), emitters 113 (emitters 113-1 through 113-$j$, where 'j' is an integer greater than '1'), and markers 114 (markers 114-1 through 114-$k$, where 'k' is an integer greater than '1') according to an embodiment. An example embodiment is described in further detail in the international application No. PCT/IB2021/061474, titled "Wearable Garment Adapted for Ultrasound Sensing and Methods Thereof for Full Wave Inversion with Imprecise Sensor Positions", assigned to common assignee, and referred to herein as the '474 patent application, and hereby incorporated by reference for all that it contains. Embedding of sensors 112, emitters 113, and markers 114 may be achieved by different techniques such as, but not limited to, weaving, gluing, mechanically attaching, and the like, and any combination thereof. The USG 110 is designed to provide an imaging solution that transmits and receives ultrasound signals that are then processed to generate a high-resolution, three-dimensional (3D) image of a scanned body part, where connectors 115, for example 115-1 and 115-2, provide the ability to secure the USG 110 around a moving medium, for example, a body part.

In an embodiment, the USG 110 may be further equipped with an electronic circuit 116 that is adapted to provide the power for consumption by the components (sensors 112, emitters 113, and/or markers 114) of the USG 110. Furthermore, the electronic circuit 116 may include a combination of digital, analog, and optical components as may be necessary for the proper operation of the USG 110. The signals received from the sensors 112 may be processed by the electronic circuit 116 locally or, after initial or minimal processing, transmitted, by wire or wirelessly to a processing circuitry (not shown) that may further process the signal and display on a display device (not shown) an image corresponding to the processed signals.

The USG 110 and its embedded components are communicatively connected (wired, wireless, or any permissible combination thereof) to a controller 101 that includes a processing circuitry (PC) 180, a memory 120, a sensor control interface (SCI), an emitter control interface (ECI) 140, a power control unit (PCU), a communication interface unit (CIU), and optionally a marker control interface (MCI). In an embodiment, the components of the controller 101 may be communicatively connected. The controller 101 is configured to control the USG 110 and its embedded components, for example, but not limited to the emitter 113. In an example embodiment, the controller 101 directs emitters 113 to stop emitting upon determining motion below a predetermined threshold value. In another example embodiment, the control 101 is adapted to activate certain emitters 113 to emit ultrasound waves to a medium.

The processing circuitry (PC) 180 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

A portion of the memory 120 may contain therein code 125, wherein when the code 125 is executed by the PC 180. The methods described herein provide the benefits of performing FWI adapted to account for a moving body tissue or organ, and as further explained in greater detail herein. The SCI 130 is adapted to at least receive, from the sensors 112, signals that are sensed by the sensors 112. The SCI 130 may receive signals in parallel from all, part, or just one of the sensors 112. The ECI 140 is adapted to at least send to the emitters 113 control signals to activate the emitters 113. The ECI 140 may transmit signals in parallel to all, part, or just one of the emitters 113.

The optional MCI 150 may be used for active markers 114 and is adapted to at least activate the active markers 114. The MCI 150 may transmit control signals in parallel to all, part, or just one of the active markers 114. The PCU 160 is adapted to provide the necessary operational power to elements (e.g., sensors 112, emitters 113, markers 114, and the like) of the USG 110 which can be done in parallel, part, or just a single element of the USG 110.

In addition, the CIU 170 is adapted to provide communications to and from the USG 110. For example, and without limitation, the CIU 170 may provide a) communication means to activate the USG 110; b) receive signals from an external device (not shown) controlling the USG 110; and c) transmit processed or raw signals captured by the sensors 112 according to any of the embodiments described herein. The PC 180 may include one or more processing circuitries without departing from the scope of the present disclosure.

At the start of the inversion process a sub-surface sound velocity model (also simply referred as a velocity model) and attenuation models are unknown. A forward simulation takes the input signals (that were sent into the body, in the case of medical ultrasound) and simulates their propagation on an initial, hypothetical, model. The output of this forward simulation represents the pressures measured on each of the sensors. The forward simulation results are compared to the actual measured values and the error therebetween is then used to modify the sound velocity model and attenuation. The process is repeated iteratively until a convergence criterion of simulation and actual results is met. At this point, the model is assumed to be a valid replica of the sub-surface structures. In order to improve the morphing model, it is necessary to update the sound velocity model and vice versa. The term sound velocity model commonly refers to the inversion of 3D data of the sound speed at each point.

It should be noted that sub-surface structures differ depending on, for example, but not limited to, part or location on the moving medium, type of medium, age of patient body, particular conditions, and the like, and any combination thereof. To this end, an accurate model increases precision in creating ultrasound images to even accommodate for minor motions that may otherwise be neglected.

A moving medium in which the waves propagate may be described by a function mapping (morphing) each point x' of the medium at time t to its original location x at time 0: $\vec{x}' = \vec{X}'_t(x)$. In an example embodiment, the medium is a body moving during measurement and altering its shape. It is assumed that the medium in which the waves travel moves slowly in time relative to the speed of sound in that medium.

The disclosed embodiments are described using an acoustic wave equation in a medium in which the density is slowly varying. However, it should be appreciated that the disclosed embodiments equally apply to variable density, elastic, and visco-elastic cases by adding the appropriate equation terms. The wave equation in the moving medium reference frame is written in terms of the Laplacian $\nabla_{x'}^2$ in the curvilinear system as:

$$\frac{1}{c^2(x',t)} \frac{d^2 P}{dt^2} - \nabla_{x'}^2 P = f(x',t) \qquad \text{Eq. 1}$$

Where P is the pressure at the medium point x' (not the real space point x), c is the speed of sound at the medium point x' (not the real space point x) and f is an external force density acting at that point. That force shall be disregarded in the following discussion.

The variation of the medium in which the waves travel can be described as a combination of spatial warping transformation and changes in elasticity. Typically, changes in the density and elasticity (or stiffness) during movement are small and so warping mainly affects the speed of sound within the medium. Specifically, using the mapping function defined above, $\vec{x}' = \vec{X}'_t(x)$, the speed of sound c(x', t) at point x' can be linearly approximated using the speed at the original point x and change in sound velocity due to changes in elasticity as shown in Equation 2.

$$c(x',t) = c(\vec{X}_t(x),0)(1 + \vec{v}(\vec{X}_t(x),t)) \qquad \text{Eq. 2:}$$

In an embodiment, it is further assumed that the time taken for an exposure, $T_f$, is short enough so that the change in the elastic constant is negligible. Furthermore, the transformation may be approximated by a linear function of time as change takes place from the initial positions to the final position. This is shown by Equation 3.

$$\vec{X}(x,t) = \frac{t}{T_f} G(x) + \left(1 - \frac{t}{T_f}\right) x \qquad \text{Eq. 3}$$

Accordingly, $\vec{X}(x, 0) = x$ and $\vec{X}(x, T_f) = G(x)$ as the final position of each unit volume of the medium. The mapping function, G(x), in an embodiment, is further assumed to be doubly differentiable. Therefore, it should be appreciated that the disclosed embodiments link morphing to the use of FWI in the field of ultrasound imaging, for example, that involves living tissue.

Data acquisition for a precise FWI is done in a series of exposures. In each exposure, a subset of ultrasound emitters produces a pulse, or a series of pulses, and a plurality of sensors records the sensed pressure for a predefined period of time. While an exposure can be relatively fast, the entire acquisition process, i.e., a set of many exposures and processing thereof, can be much slower.

Given a mapping function G(x), model parameters are computed using a slightly modified FWI scheme. First, the forward simulation is carried out by the use of parameters of a time dependent model. Second, the calculation of the misfit gradient, with respect to the model at each FWI iteration, changes to reflect the morphing change. This is further explained herein. The modified forward simulation reflects the changed equation of motion. Specifically, the discrete version of Equation 1 is shown in Equation 4.

$$P_{i,j}^{n+1} = 2 P_{i,j}^n - P_{i,j}^{n-1} + \left(c \frac{\Delta t}{\Delta h}\right)^2 \sum b_{i'j'} P_{i+i',j+j'}^n \qquad \text{Eq. 4}$$

Here, $\Delta t$, $\Delta h$ are the steps in time and space, respectively, and $P_{i,j}^n$ is the pressure at grid cells i,j at time, $t = n\Delta t$, and $b_{i',j'}$ are finite-difference constants for integration in curvilinear coordinates and are a function of G(x) and time t.

The real measured pressure at the sensors is matched with the simulated pressure to evaluate a misfit error functional. This error is injected back into the medium and is propagated back in time by using an adjoint wave equation, in order to compute the effect of every single point in the medium on the misfit error. Then, the misfit error gradient with respect to the model parameter c(x) can be computed, leading to Equation 6:

$$\frac{\partial E}{\partial c(x',t)} = -\int \frac{2J(x')}{c(x',t)} (P^\dagger \nabla_{x'}^2 P) \frac{\partial c(x',t)}{\partial c_0(x)} dt \qquad \text{Eq. 6}$$

J is a Jacobian of the $\vec{X}_t(x)$, P† is an adjoint wavefield, and $c_0(x)$ is a sound speed at time t=0 (see Eq. 2). Eq. 6 has a similar form to the conventional gradient with additional terms.

The disclosed embodiments as described herein are focused on a transformation function $\vec{X}_t(x, t)$ that is continuous in time and varies during the entire data acquisition session. However, in many practical applications, and embodiments thereof, this constraint can be further relaxed. As noted herein, data acquisition for FWI includes many "shot experiments", wherein, during each shot time, a subset of the emitters is activated and measured. The time of a single shot is relatively short, so that the transformation function can be considered constant during each shot time and varying only between shots. That is, within a particular shot experiment, the transformation function $\vec{X}_t(x, t)$ is constant as shown in Equation 7.

$$\vec{X}(x,i) = \frac{i\Delta t_{shot}}{T_f} G(x) + \left(1 - \frac{i\Delta t_{shot}}{T_f}\right) x \qquad \text{Eq. 7}$$

According to one embodiment, the change is viewed as a simple morphing from an initial image (i.e., a starting model) to a final image (i.e., an end model). Accordingly, x'=G(x) maps each point x in space at time t=0 to another point x' in space at time T. The assumption made is that the morphing function is linear in time. That is, the mapped point travels in a straight line from a start position to an end position. Another assumption is that the change is less than a wavelength during the time it takes to travel through the body. It should be noted that an entire FWI sequence can be longer and processed according to the present disclosure.

The G(x) is built in two steps: first, an initial estimation is produced from the data; second, the model is improved during the recurring FWI stage. The initial G(x) is estimated from predetermined constraints on specific points at the beginning and end times of movement. The points are calculated from specific signals and specific emissions intermingled in the FWI data acquisition.

There are several sources of the predetermined constraints that can be used for generating the initial G(x): a) the relative movement of emitters and sensors to their original position, noting that though the absolute position may contain a large error, the change, originating from a change in time of flight of the signal, has a fairly small error; b) certain surfaces inside the imaged body produce large echoes. e.g., muscle-bone interface, therefore, points on those surfaces can be structurally interpreted using conventional imaging techniques, such as reverse time migration; and, c) accumulated knowledge from tracking signals over time, where certain types of motions, such as breathing, can be deduced by using machine learning (ML) of the signals' patterns.

The G(x) can be reconstructed, or otherwise interpolated, from these constraints by various of methods of elastic registration and shape deformation that are adapted for use as described herein. In an embodiment, the constraints are viewed to have a larger uncertainty (rather than being exact) that need to be incorporated into building G(x) and is refined only later during the FWI. Moreover, under the assumption that the overall acquisition time is short enough for G(x) to describe small movement changes, G(x) can be viewed as being locally linear at the vicinity of the constraint points. Therefore, G(x) can be represented as shown in Equation 8.

$$G(x) = \sum_i^n \frac{(x - p_i) \cdot A_i + B_i}{\|x - p_i\|} / \sum_i^n \frac{1}{\|x - p_i\|} \qquad \text{Eq. 8}$$

Where $p_i$ is the ith constraint point and $g_i=(x-p_i) \cdot A_i + B_i$ is the linear transformation of that point. The constants $A_i$, $B_i$ vectors can be found by minimization.

Figure 2:
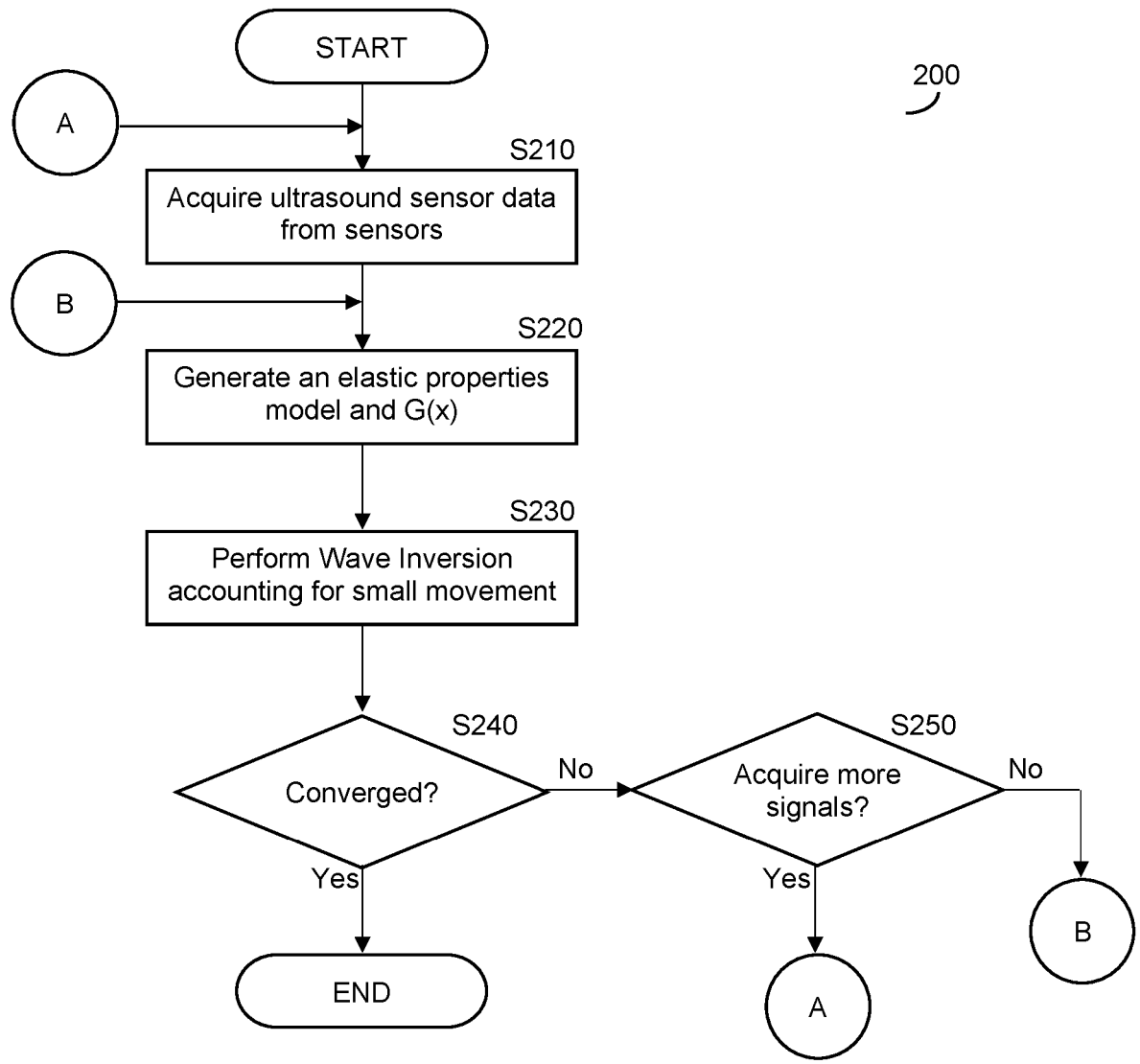
FIG. 2 is a flowchart of performing acquisition, modeling, and a waveform inversion for creating an ultrasound image of a moving medium according to an embodiment.

FIG. 2 is an example flowchart 200 of performing data acquisition, modeling, and full waveform inversion (FWI) in a moving medium according to an embodiment. In an embodiment, an input to a FWI iteration is a model of elastic properties and a morphing function, and the output is an updated model of elastic properties and morphing function. According to an embodiment, there are three distinct parts to finding the morphing function, G(x), and the model: a) the system uses raw signals to find some initial approximation of G(x); b) inversion techniques such as, FWI, to compute an approximate model of elastic properties given the initial morphing function; and, c) the system improves G(x) by solving the inverse problem of G(x) given the model of elastic properties. The last 2 steps above are repeated until both G(x) and the model of elastic properties converge. At the system level, during signal acquisition, a code is used to find the first approximation of G(x) from raw signals to restart the acquisition process if a large movement has been registered.

Figure 3:
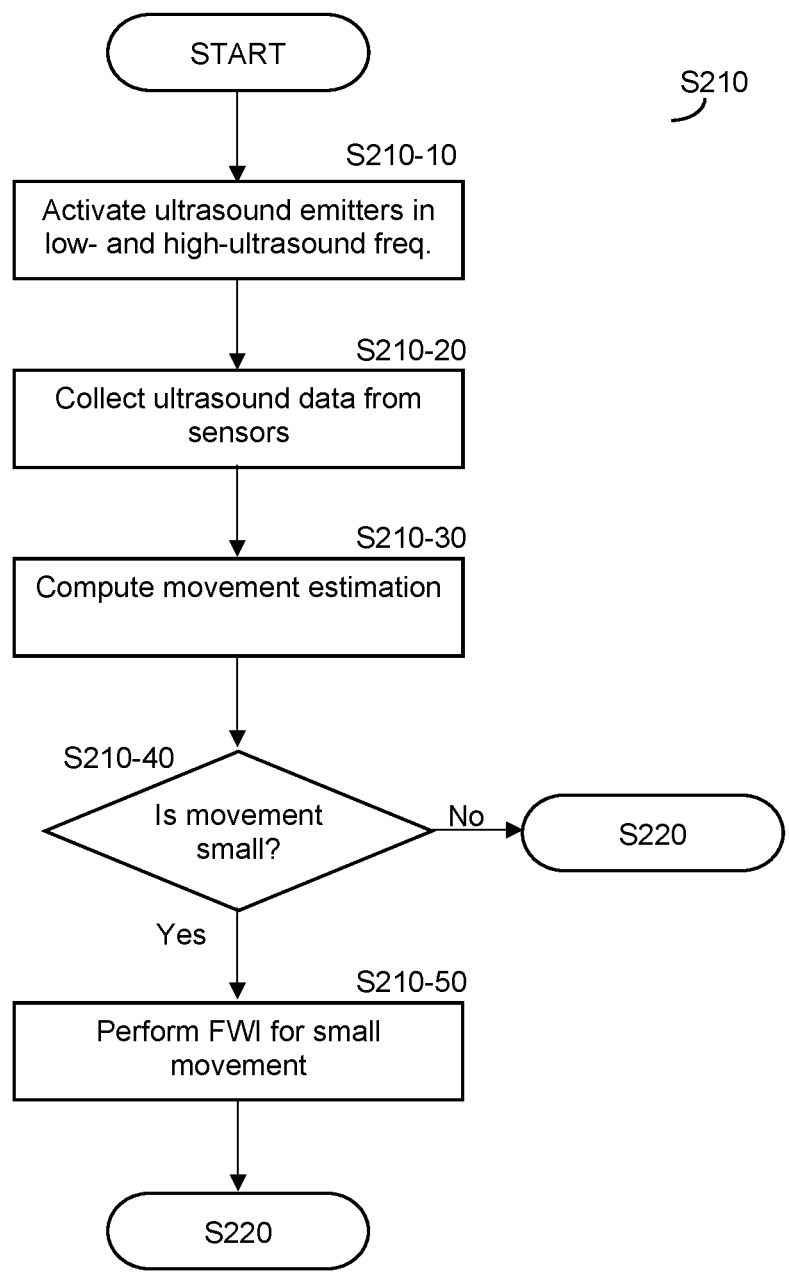
FIG. 3 is a flowchart of performing an acquisition stage of the waveform inversion in a moving medium according to an embodiment.

At S210, ultrasound signals are acquired and is described in more details in FIG. 3. Here, sensor data is collected, and movement of the moving medium is estimated. If the data collected is within a predetermined range for use by the next processing step, then execution continues with S220. In an embodiment, the predetermined range is defined as deviations in the estimated movement.

At S220, an initial elastic properties model and a G(x) (i.e., a morphing function) is generated. The model and the morphing function are later used to perform the FWI according to the principles of the disclosed embodiment. In an embodiment, a model of the morphing function accounts for the elastic properties and the morphing function. The generation is further described in FIG. 4. Once G(x) is available then execution continues with S230.

At S230, a FWI process is performed. The FWI takes accounts for motion of the moving medium, for example, but not limited to, body tissues, organs, or the like. In an embodiment, model parameters may be updated as further explained with respect to FIG. 5. The FWI may reiterate as necessary and once iterations are complete, execution continues with S240. In an embodiment, the FWI process is performed on the generated model of elastic properties and the G(x) in order to refine the generated model and morphing function.

At S240, it is checked if convergence has been achieved, i.e., if changes are below a predetermined threshold value, and if so, execution completes; otherwise, execution continues with S250. The convergence is determined in at least one of: between the generated model and a precedent model and between the generated G(x) and the precedent G(x). In an embodiment, threshold values are predetermined for the model and the G(x), respectively. A small convergence indicates close similarity between the compared models. In an embodiment, the generated model is designated as the precedent model before execution continues with S250. The 'precedent' model is the model generated in a previous round of generation and inversion which similarly applies to the 'precedent' morphing function. In an embodiment, the precedent model is updated or replaced by the generated model from the iteration of steps S220 to S240.

At S250, it is checked whether additional acquisition of ultrasound signals is necessary and if so, execution continues with S210; otherwise, execution continues with S220. In an example embodiment, additional acquisition is taken when the change in S240 is substantially large, e.g., above a predefined standard value.

In an embodiment, the generated elastic properties model and the morphing function are utilized to create an initial ultrasound image that compensates the small movements in the moving medium. In a further embodiment, subsequent ultrasound images are generated based on the initial ultrasound image created to include morphing considerations. It should be appreciated that a morphing model is generated from the onset and prior to having the initial ultrasound image. Therefore, establishing an image before ultrasound signal acquisition is not needed. In a further embodiment, the morphing model may be continuously updated to improve accuracy of initial ultrasound images being generated.

FIG. 3 is an example flowchart S210 of performing an acquisition stage of the full wave inversion (FWI) in a moving medium according to an embodiment. The method further describes S210 of FIG. 2 illustrating a method for acquiring ultrasound signals.

At S210-10, one or more emitters are activated. In an embodiment, the emitters (e.g., the emitter 113, FIG. 1) are activated using both lower and higher ranges of ultrasound frequencies. In an embodiment, a selected portion of emitters are activated. In a further embodiment, the selected portion of emitters may differ between consecutive rounds of generating a model and the morphing function. For example, emitters 1 through 10 are activated to emit ultrasound waves to acquire signals for the first G(x) and model generation and emitters 11-20 are activated to emit ultrasound waves for the second G(x) and model generation.

In S210-20, ultrasound data are collected. The ultrasound data are reflected and/or refracted ultrasound signals that are collected by sensors (e.g., the sensors 112. FIG. 1). In an embodiment, a selected portion of sensors may be utilized to collect signals emitting by the selected portion of emitters. In a further embodiment, the selected portion of sensors may be predefined for consecutive cycles of G(x) and model generation.

At S210-30, a motion estimation is computed to determine actual movements that may have occurred. The actual movements may be of, for example, but is not limited to, tissues, bones, muscles, organs, and the like, and any combination thereof.

At S210-40, it is checked whether the motion is small enough. In an embodiment, the small enough motion is a motion smaller than a predetermined displacement. If so, execution continues with S210-50; otherwise, execution terminates and continues to S220 of FIG. 2.

At S210-50, a FWI accounting for the small enough motion is performed. The execution ends and continues with S220 of FIG. 2 as described herein.

According to an embodiment, calibration shots are interleaved during FWI acquisition, for example but not by way of limitation, approximately every 100 m-second. In an example embodiment, received sensing signals are registered as being similar to the initial sensing signal when determined that the body did not move based on the calibration shots. The selected emitters for the calibration process are at predetermined locations on the surface of the USG 110 that are in the vicinity of bone edges which provide a distinct reflected signal, and which are more sensitive to movement. In an embodiment, collected ultrasound data (i.e., signals) are discarded when the movement detected during calibration is beyond a threshold value. In a further embodiment, acquisition cycle continues upon discarding the ultrasound data. Hence the activation of emitters in S210-10 should be understood as activation which may include also the calibration signals from the designated emitters.

Figure 4:
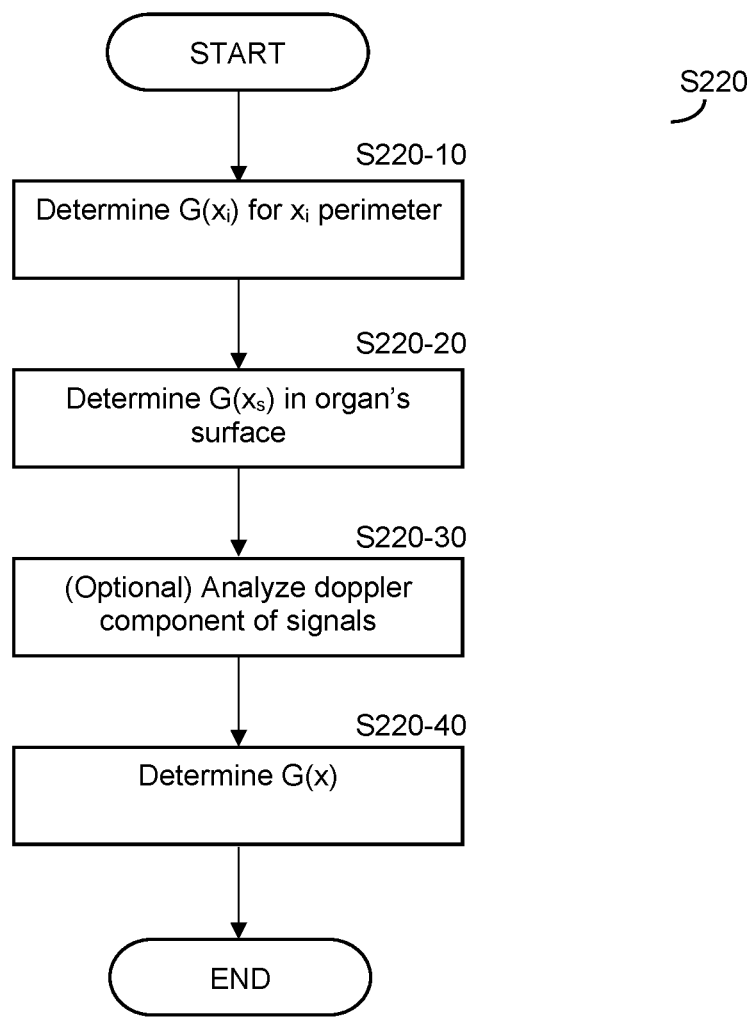
FIG. 4 is a flowchart of generating a model and a morphing function of a waveform inversion in a moving medium according to an embodiment.

FIG. 4 is an example flowchart S220 illustrating a method for generating an initial model and a morphing function, G(x), of a FWI in a moving medium according to an embodiment.

In S220-10, $G(x_i)$ for $x_i$ on perimeter is determined based on signals collected by sensor's (e.g., the sensors 112, FIG. 1) relative location.

At S220-20, $G(x_s)$ on an organ's surface is determined based on an echo (e.g., ultrasound signals) which is based on conventional imaging techniques.

At S220-30, optionally, a Doppler signal component may be analyzed to provide higher imaging accuracy.

At S220-40, G(x) is determined. In one embodiment, the G(x) is interpolated from given constraints. In another embodiment, the G(x) is determined by applying an algorithm, for example, a machine learning algorithm, based on previous G(x) estimations and received signal data. The method to determine G(x) may be selected automatically or manually, without combining.

Figure 5:
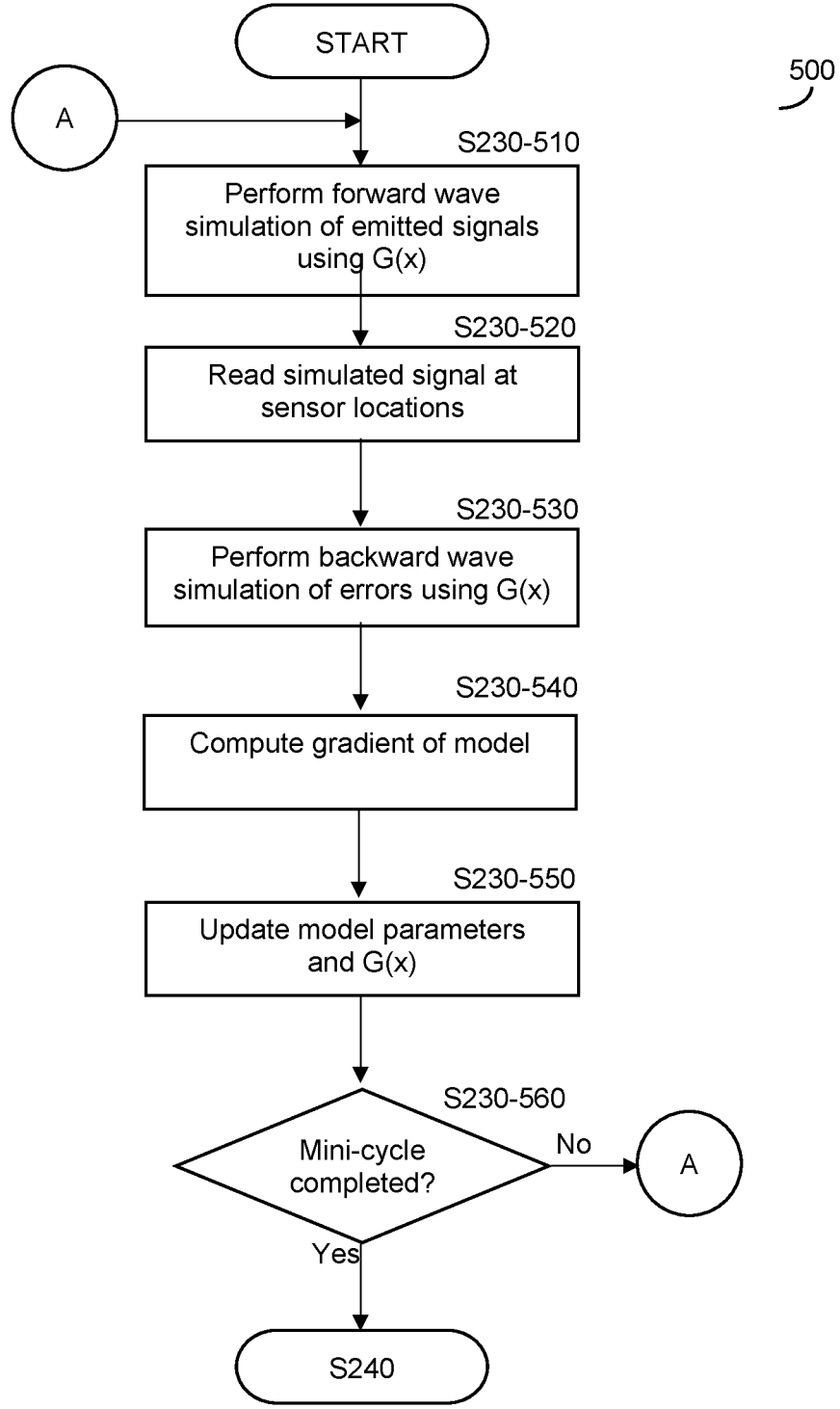
FIG. 5 is a flowchart of performing a full waveform inversion (FWI) in a moving medium according to an embodiment.
Figure 6:
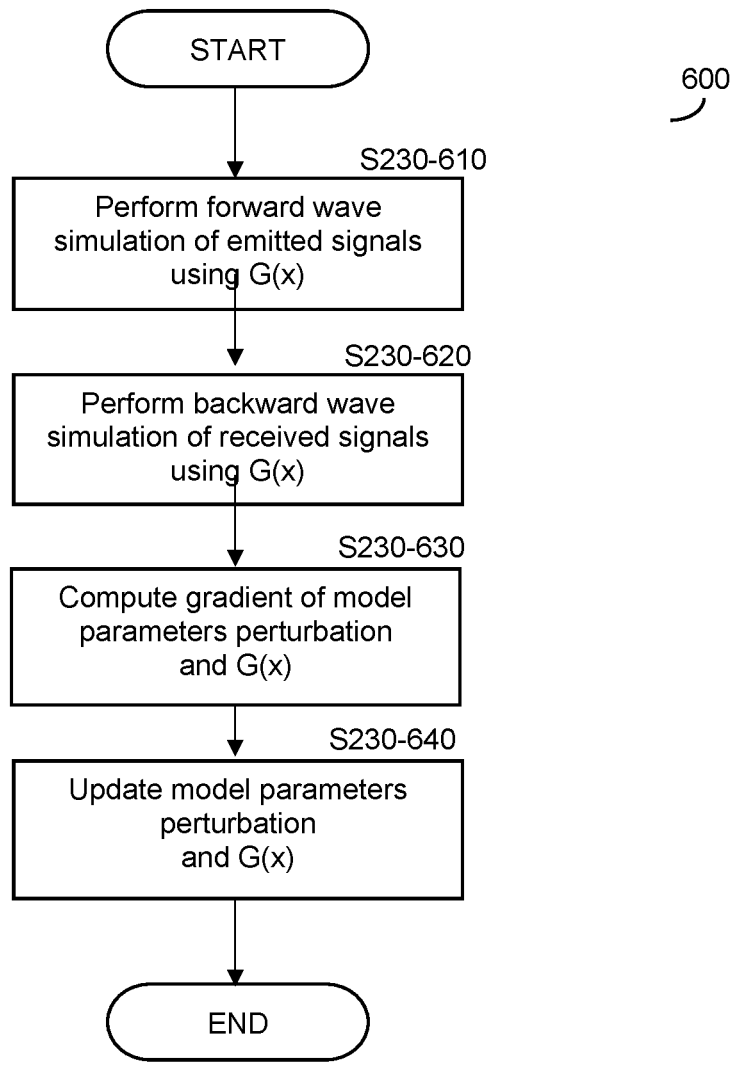
FIG. 6 is a flowchart of performing a reverse time migration (RTM) in a moving medium according to an embodiment.
Figure 7:
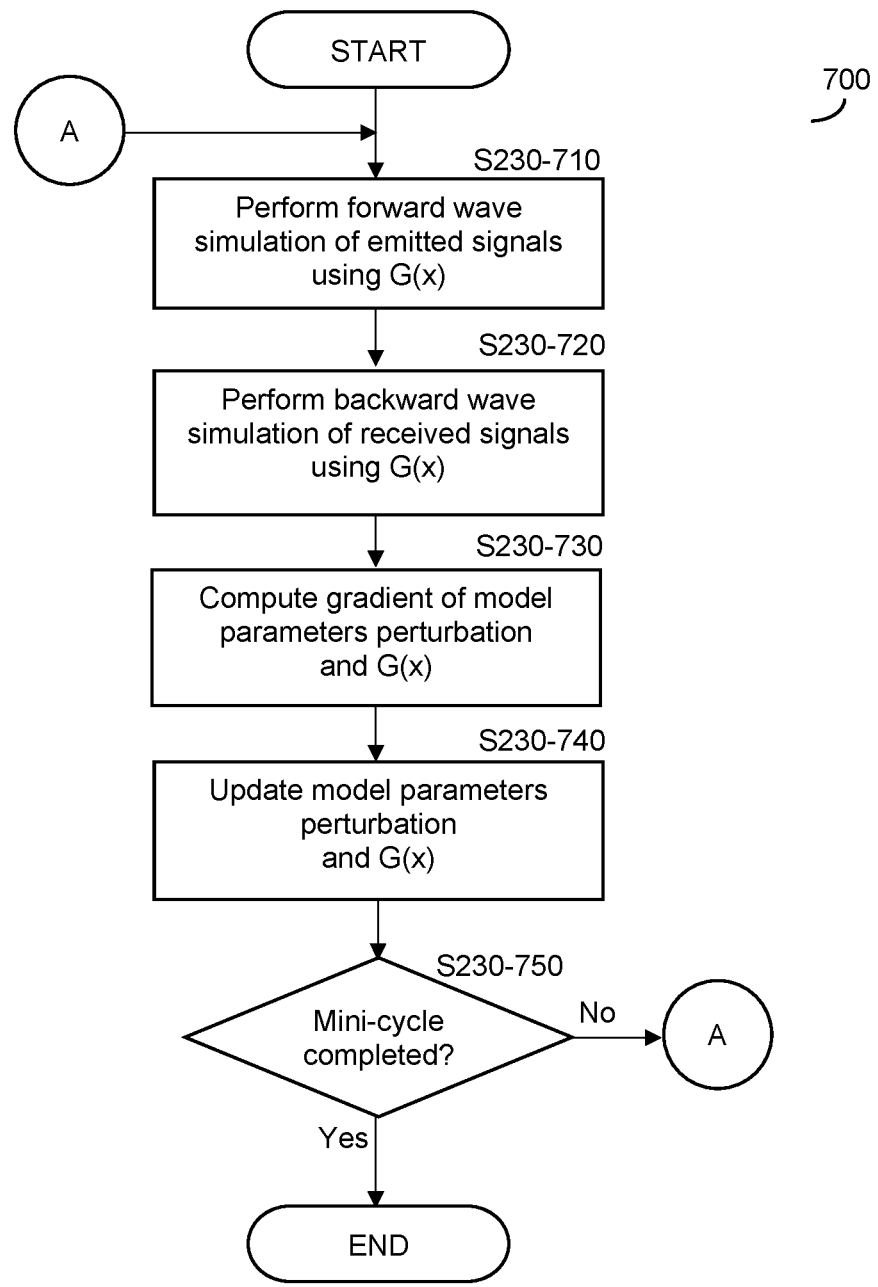
FIG. 7 is a flowchart of performing a least-squares migration (LSM) in a moving medium according to an embodiment.

FIGS. 5, 6, and 7 show examples of different embodiments of S230 of FIG. 2 to perform FWI. FIG. 5 is an example flowchart 500 of performing full waveform inversion (FWI) in a moving medium according to one embodiment. At S230-510, forward wave simulation (FWI) of emitted signals is performed. In S230-520, simulated signals at sensor locations are read. At S230-530, backward wave simulation of errors is performed. At S230-540, gradient of model is computed. At S230-550, model parameters and G(x) are updated. At S230-560, it is checked if a mini-cycle has completed and if not, execution continues with S230-510; otherwise, execution terminates and continues to S240 of FIG. 2 as described herein. In an example embodiment, a complete mini-cycle is identified by determining convergence of the input and output models of the FWI processes below a predetermine standard value.

FIG. 6 is an example flowchart 600 of performing reverse time migration (RTM) in a moving medium according to another embodiment. At S230-610, a forward wave simulation of emitted signals is performed. The forward simulation is done in curvilinear coordinates according to equation 1 using G(x). At S230-620, a backward wave simulation of the received signals is performed. The backwards simulation again uses G(x) to address movement. At S230-630, the gradient of the model is computed as in Eq. 6 (P† is now the back propagated received signals instead of the errors). At S230-640, the perturbation of model parameters is updated. Thereafter, execution of S230 finishes and S240 of FIG. 2 takes place as described herein.

FIG. 7 is an example flowchart 700 of performing a least-square migration (LSM) in a moving medium according to yet another embodiment. At S230-710, a forward wave simulation of emitted signals is performed. The forward simulation is done in curvilinear coordinates according to equation 1 using G(x). At S230-720, a backward wave simulation of received signals is performed. The backwards simulation again uses G(x) to compensate movements. At S230-730, the gradient of the model is computed as in Eq. 6 (P† is now the back propagated received signals instead of the errors). At S230-640, the perturbation of model parameters is updated. At S230-750, it is checked if a mini-cycle has completed and if not, execution continues with S230-710; otherwise, execution finishes, and S240 of FIG. 2 takes place as described herein.

Hence an aspect of the disclosed embodiment is of a computerized method for generation of a morphing function for use in creation of ultrasound images of a moving medium, the method comprising: emitting by a first plurality of emitters a first plurality of ultrasound waves towards a body of a patient; receiving by a first plurality of sensors a first plurality of received signals corresponding to the first plurality of ultrasound waves; determining based on at least a first received signal of the first plurality of received signals that motion of the medium is below a predetermined threshold and if so continuing or otherwise, discarding the first plurality of received signals and repeating the emitting by a first plurality of emitters and receiving by a first plurality of sensors; emitting by a second plurality of emitters a second plurality of ultrasound waves towards a body of a patient; receiving by a second plurality of sensors a second plurality of received signals corresponding to the second plurality of ultrasound waves; determining based on at least a second received signal of the second plurality of received signals that motion of the medium is below a predetermined threshold and if so continuing or otherwise, discarding the second plurality of received signals and repeating the emitting by a second plurality of emitters and receiving by a second plurality of sensors; and, generating a model of the morphing function, wherein the morphing function establishes a morphing of the moving medium between the first plurality of received signals and the second plurality of received signals.

Other aspects of the computerized method include but are not limited to: the plurality of ultrasound waves comprises at least an ultrasound wave emitted from a first emitter of the plurality of emitters that is designated as a calibration emitter; the designation of the first emitter of the plurality of emitters is based on determination of proximity of the first emitter to a reflecting element; the reflecting element is an edge of a bone within a body; the motion is determined based on the reflection received from the reflecting element; generating a sound velocity model based on the generated morphing model; the plurality of received signals is one of: reflected signals, refracted signals, and combinations thereof; generating at least an initial ultrasound image using the generated morphing model; and, repeating emitting by a first plurality of emitters, receiving by a first plurality of sensors, determining based on at least a first received signal, emitting by a second plurality of emitters, receiving by a second plurality of sensors, determining based on at least a second received signal, and generating a model of the morphing function.

The teachings herein may be further embodied in a system that comprises: a processing element; a plurality of ultrasound emitters adapted to emit an ultrasound wave under control of the processing element, wherein the plurality of ultrasound emitters are assembled within a wearable garment; a plurality of ultrasound sensors adapted to send readings corresponding the ultrasound waves received by the plurality of ultrasound sensors, wherein the plurality of ultrasound sensors are assembled within a wearable garment and placed among the plurality of ultrasound emitters; and, a memory communicatively connected to the processing elements and containing therein a plurality of instructions that when executed by the processing element cause the system to: emit by a first plurality of emitters of the plurality of ultrasound emitters a first plurality of ultrasound waves towards a body of a patient; receive by a first plurality of sensors of a plurality of ultrasound sensors a first plurality of received signals corresponding to the first plurality of ultrasound waves; determine based on at least a first received signal of the first plurality of received signals that motion of the medium is below a predetermined threshold and if so continue or otherwise, discard the first plurality of received signals and repeating the emitting by a first plurality of emitters and receiving by a first plurality of sensors; emit by a second plurality of emitters of the plurality of ultrasound emitters a second plurality of ultrasound waves towards a body of a patient; receive by a second plurality of sensors of the plurality of ultrasound sensors a second plurality of received signals corresponding to the second plurality of ultrasound waves; determine based on at least a second received signal of the second plurality of received signals that motion of the medium is below a predetermined threshold and if so continue or otherwise, discard the second plurality of received signals and repeating the emitting by a second plurality of emitters and receiving by a second plurality of sensors; and, generate a model of the morphing function, wherein the morphing function establishes a morphing of the moving medium between the first plurality of received signals and the second plurality of received signals.

Other aspects of the system include but are not limited to: the plurality of ultrasound emitters are sparsely placed upon the wearable garment; the plurality of ultrasound sensors are sparsely placed upon the wearable garment; at least one of the plurality of ultrasound emitters and the plurality of ultrasound sensors is embodied in a single device; the plurality of ultrasound waves further comprises at least an ultrasound wave emitted from a first emitter of the plurality of emitters that is designated as a calibration emitter; designation of the first emitter of the plurality of emitters is based on determination of proximity of the first emitter to a reflecting element; the reflecting element is an edge of a bone within a body; the motion is determined based on the reflection received from the reflecting element; the memory further contains instructions that when executed by the processing element generates a sound velocity model based on the generated morphing model; the plurality of received signals is one of: reflected signals, refracted signals, and combinations thereof; the memory further contains instructions that when executed by the processing element generates at least an initial ultrasound image using the generated morphing model; and, the memory further contains instructions that when executed by the processing element: repeats emitting by a first plurality of emitters, receives by a first plurality of sensors, determines based on at least a first received signal, emits by a second plurality of emitters, receives by a second plurality of sensors, determine based on at least a second received signal, and generate a model of the morphing function.

Further aspects of an inversion method for analysis of ultrasound waves received from a moving medium include, but are not limited to, receiving ultrasound wave data from a plurality of ultrasound sensors; simulating the ultrasound wave in the moving medium using at least a morphing function; and updating at least an elastic property of the moving body based on at least the simulation. In yet another aspect the simulation further comprises at least one of: a forward simulation and a backward simulation. In yet another aspect of the invention the simulation comprises: full waveform inversion (FWI), adaptive waveform inversion (AWI), physically based deep neural networks (DNN)

inversion, Least Squares Migration (LSM), one-way wave equation migration, two-way wave equation migration, reverse time migration (RTM), and any combination thereof.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), general purpose compute acceleration device such as graphics processing units ("GPU"), a memory, and input/output interfaces. The computer platform may also include an operating system and microinstruction code. The various processes and functions described herein may be either part of the microinstruction code or part of the application program, or any combination thereof, which may be executed by a CPU or a GPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for creating ultrasound images of a moving medium by generating a morphing function, comprising:
    emitting, by a portion of a plurality of emitters, a plurality of ultrasound waves until a motion of the moving medium below a predetermined threshold is determined, wherein the plurality of ultrasound wave is emitted towards the moving medium;
    receiving, by a portion of a plurality of sensors, a first plurality of received signals corresponding to the plurality of ultrasound waves;
    generating a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and
    performing a wave inversion on the model of the morphing function.

2. The method of claim 1, further comprising:
    comparing the model of the morphing function with a precedent model, wherein the precedent model is determined prior to generation of the model of the morphing function;
    determining, based on the comparison, a convergence between the precedent model and the model of the morphing function; and
    updating the precedent model with the model of the morphing function when the convergence is greater than a predetermined value.

3. The method of claim 2, wherein the portion of the plurality of emitters is a first portion of the plurality emitters and the portion of the plurality of sensors is a first portion of the plurality of sensors, and wherein the convergence is greater than the predetermined value, further comprising:
    repeating the emitting, by a second portion of the plurality of emitters, and the receiving, by a second portion of the plurality of sensors, wherein a second plurality of received signals are received; and
    repeating the generating the model of the morphing function and the performing a wave inversion, wherein the morphing function defines morphing of the moving medium from the first plurality of received signal.

4. The method of claim 1, further comprising:
    emitting, by an initial portion of the plurality of emitters, an initial plurality of ultrasound waves until an initial motion of the moving medium below the predetermined threshold is determined; and
    receiving, by an initial portion of a plurality of sensors, the initial plurality of received signals corresponding to an initial plurality of ultrasound waves, wherein the initial motion of the medium is determined based on at least the initial plurality of received signals.

5. The method of claim 2, further comprising:
    generating at least one ultrasound image using the model of the morphing function.

6. The method of claim 1, further comprising:
    generating a sound velocity model based on the generated model of the morphing function.

7. The method of claim 1, wherein the plurality of received signals is any one of: reflected signals and refracted signals.

8. The method of claim 1, wherein performing the wave inversion further comprises:
    simulating the plurality of received signals using the morphing function, wherein the morphing function is determined based on the model of the morphing function; and
    iteratively updating at least an elastic property of the moving medium and the morphing function based on at least the simulation.

9. The method of claim 8, wherein the simulation of the plurality of received signals include at least one of: a forward simulation and a backward simulation.

10. The method of claim 1, wherein the wave inversion includes any one of: full waveform inversion (FWI), adaptive waveform inversion (AWI), physically based deep neural networks (DNN) inversion.

11. The method of claim 1, wherein the portion of the plurality of emitters include at least one designated calibration emitter, wherein the at least one calibration emitter is located proximal to a reflecting element of the moving medium.

12. A system for ultrasound imaging of a moving medium, the system comprising:
- a processing circuitry;
- a plurality of ultrasound emitters adapted to emit an ultrasound wave under control of the processing circuitry;
- a plurality of ultrasound sensors adapted to send readings corresponding the ultrasound waves received by the plurality of ultrasound sensors; and
- a memory communicatively connected to the processing circuitry and containing therein a plurality of instructions that when executed by the processing circuitry, configure the system to:
- emit, by a portion of a plurality of emitters, a plurality of ultrasound waves until a motion of the moving medium below a predetermined threshold is determined, wherein the plurality of ultrasound wave is emitted towards the moving medium;
- receive, by a portion of a plurality of sensors, a first plurality of received signals corresponding to the plurality of ultrasound waves;
- generate a model of a morphing function when the motion of the moving medium is below the predetermined threshold, wherein the motion of the moving medium is determined based on at least one received signal of the plurality of first received signals, wherein the morphing function defines morphing of the moving medium from an initial plurality of received signals; and
- perform a wave inversion on the model of the morphing function.

13. The system of claim 12, wherein the system is further configured to: comparing the model of the morphing function with a precedent model, wherein the precedent model is determined prior to generation of the model of the morphing function;
- determine, based on the comparison, a convergence between the precedent model and the model of the morphing function; and
- update the precedent model with the model of the morphing function when the convergence is greater than a predetermined value.

14. The system of claim 13, wherein the portion of the plurality of emitters is a first portion of the plurality emitters and the portion of the plurality of sensors is a first portion of the plurality of sensors, wherein the convergence is greater than the predetermined value, and wherein the system is further configured to:
- repeat the emitting, by a second portion of the plurality of emitters, and the receiving, by a second portion of the plurality of sensors, wherein a second plurality of received signals are received; and
- repeat the generating the model of the morphing function and the performing a wave inversion, wherein the morphing function defines morphing of the moving medium from the first plurality of received signal.

15. The system of claim 12, wherein the system is further configured to:
- emit, by an initial portion of the plurality of emitters, an initial plurality of ultrasound waves until an initial motion of the moving medium below the predetermined threshold is determined; and
- receive, by an initial portion of a plurality of sensors, the initial plurality of received signals corresponding to an initial plurality of ultrasound waves, wherein the initial motion of the medium is determined based on at least the initial plurality of received signals.

16. The system of claim 13, wherein the system is further configured to: generate at least one ultrasound image using the model of the morphing function.

17. The system of claim 12, wherein the system is further configured to: generate a sound velocity model based on the generated model of the morphing function.

18. The system of claim 12, wherein the plurality of received signals is any one of: reflected signals and refracted signals.

19. The system of claim 12, wherein the system is further configured to:
- simulate the plurality of received signals using the morphing function, wherein the morphing function is determined based on the model of the morphing function; and
- iteratively update at least an elastic property of the moving medium and the morphing function based on at least the simulation.

20. The system of claim 19, wherein the simulation of the plurality of received signals include at least one of: a forward simulation and a backward simulation.

21. The system of claim 12, wherein the wave inversion includes any one of: full waveform inversion (FWI), adaptive waveform inversion (AWI), physically based deep neural networks (DNN) inversion.

22. The system of claim 12, wherein the portion of the plurality of emitters include at least one designated calibration emitter, wherein the at least one calibration emitter is located proximal to a reflecting element of the moving medium.

\* \* \* \* \*